US006426507B1

(12) United States Patent
Rangwalla et al.

(10) Patent No.: US 6,426,507 B1
(45) Date of Patent: Jul. 30, 2002

(54) PARTICLE BEAM PROCESSING APPARATUS

(75) Inventors: Imtiaz Rangwalla, Andover; Harvey Clough, North Andover, both of MA (US); George Hannafin, Hudson, NH (US)

(73) Assignee: Energy Sciences, Inc., Wilmington, MA (US)

( * ) Notice: Subject to any disclaimer, the term of this patent is extended or adjusted under 35 U.S.C. 154(b) by 0 days.

(21) Appl. No.: 09/434,380

(22) Filed: Nov. 5, 1999

(51) Int. Cl.[7] .......................... A61N 5/00; G21G 5/00; H05H 7/00

(52) U.S. Cl. .......................... 250/492.3; 315/506

(58) Field of Search .......................... 250/492.3; 315/506

(56) References Cited

U.S. PATENT DOCUMENTS

| | | | |
|---|---|---|---|
| 3,440,466 A | 4/1969 | Colvin et al. | |
| 3,925,670 A | 12/1975 | Farrell et al. | |
| 4,143,468 A | 3/1979 | Novotny et al. | |
| 4,210,813 A | 7/1980 | Romanovsky et al. | |
| 4,248,665 A | 2/1981 | Thode | |
| 4,323,780 A | 4/1982 | Tombaugh et al. | |
| 4,323,858 A | 4/1982 | Gerstley | |
| 4,324,980 A | 4/1982 | Symmons | |
| 4,446,374 A | 5/1984 | Ivanov et al. | |
| 4,507,614 A | 3/1985 | Prono et al. | |
| 4,845,370 A | 7/1989 | Thompson et al. | |
| 4,952,814 A | 8/1990 | Huntzinger | |
| 5,051,600 A | 9/1991 | Schuetz et al. | |
| 5,175,436 A | 12/1992 | Puumalainen | |
| 5,416,440 A | 5/1995 | Lyons et al. | |
| 5,489,783 A * | 2/1996 | Kristiansson | 250/442.3 |
| 5,530,255 A | 6/1996 | Lyons et al. | |
| 5,561,298 A | 10/1996 | Cirlin et al. | |
| 5,603,972 A | 2/1997 | McFarland | |
| 5,801,387 A | 9/1998 | Nablo et al. | |
| 5,898,261 A | 4/1999 | Barker | |
| 5,962,995 A | 10/1999 | Avnery | |

FOREIGN PATENT DOCUMENTS

| | | |
|---|---|---|
| EP | 99 35665 | 7/1999 |
| FR | 2.114.927 | 6/1972 |
| GB | 1 140 694 | 1/1969 |

OTHER PUBLICATIONS

International Search Report dated Dec. 28, 2000.

* cited by examiner

*Primary Examiner*—Jack Berman
*Assistant Examiner*—Johnnie L Smith, II
(74) *Attorney, Agent, or Firm*—Finnegan Henderson Farabow Garrett & Dunner, L.L.P.

(57) ABSTRACT

The present invention is directed to a particle beam processing apparatus that is smaller in size and operates at a higher efficiency. The processing apparatus includes a particle beam generating assembly, a foil support assembly, and a processing assembly. In the particle beam generating assembly, a cloud of particles, for example, electrons, are generated by heating at least one tungsten filament. The electrons are then extracted to travel at a high speed to the foil support assembly which is set at a much lower voltage than the particle beam generating assembly. A substrate is fed to the processing apparatus through the processing zone and is exposed to the electrons exiting the particle beam generating assembly and entering the processing zone. The electrons penetrate and cure the substrate causing a chemical reaction, such as polymerization, cross-linking, or sterilization.

13 Claims, 10 Drawing Sheets

PARTICLE BEAM PROCESSING APPARATUS

BACKGROUND OF THE INVENTION

1. Field of the Invention

This invention relates to a particle beam processing apparatus. In particular, this invention relates to a particle beam processing apparatus including a particle generating assembly, a foil support assembly having a thin foil, and a processing zone to cause a chemical reaction on a substrate or a coating.

2. Description of the Related Art

A particle beam processing device is commonly used to expose a substrate or coating to highly accelerated particle beams, such as an electron beam (EB), to cause a chemical reaction on the substrate or coating.

An electron is a negatively charged particle found in all matter. Electrons revolve around the nucleus of an atom much like planets revolve around the sun. By sharing electrons, two or more atoms bind together to form molecules. In EB processing, electron beams are used to modify the molecular structure of a wide variety of products and materials. For example, electrons can be used to alter specially designed liquid coatings, inks and adhesives. During EB processing, electrons break bonds and form charged particles and free radicals. These radicals then combine to form large molecules. By this process, the liquid is transformed into a solid. This process is known as polymerization.

Liquid coatings treated with EB processing may include printing inks, varnishes, silicone release coatings, primer coatings, pressure sensitive adhesives, barrier coatings and laminating adhesives. EB processing may also be used to alter and enhance the physical characteristics of solid materials such as paper, plastic films and non-woven textile substrates, all specially designed to react to EB treatment.

A particle beam processing device generally includes three zones. They are a vacuum chamber zone where particle beam is generated, a particle accelerator zone, and a processing zone. In the vacuum chamber, tungsten filament is heated to about 2400 K, which is the electron emission temperature of tungsten, to create a cloud of electrons. A positive voltage differential is then applied to the vacuum chamber to extract and simultaneously accelerate these electrons. Thereafter the electrons pass through a thin foil and enter the processing zone. The thin foil functions as a barrier between the vacuum chamber and the processing zone. Accelerated electrons exit the vacuum chamber through the thin foil and enter the processing zone at atmospheric conditions.

Electron beam processing devices that are commercially available at the present time generally operate at a minimum voltage of 125 kVolts. These existing EB units utilize thin foil made of titanium having a thickness of 12.5 micrometers, to cure coatings on substrates that are being fed through the processing devices at a rate of 800–1000 feet per minute. For example, such an EB unit may be purchased from Energy Sciences, Inc. of Wilmington, Mass., Model No. 125/105/1200. However, these processing devices do not function efficiently because most of the energy from the 125 kVolts is wasted. In addition, the current technology cannot be used in certain industries like flexible food packaging. An EB unit operating at 125 kVolts deposits substantial amounts of the energy onto the polyethylene based sealant films which contact the food being packaged. This deposit causes off-odors in the films and increases its seal initiation temperatures.

One way to increase the efficiency is by reducing the operating voltage below 125 kVolts. In addition, operating below 125 kVolts allows better control of the depth of energy deposition and minimizes the electron energy absorbed by the sealant films. However, when the voltage is reduced below 125 kVolts, the kinetic energy of the electrons traveling through the titanium foil decreases because more energy is being absorbed by the titanium foil, causing the foil to heat up excessively. Excessive heat causes the titanium foil to become blue, brittle, and lose its mechanical strength. Excessive heat also poses a problem with heat management of the system. Consequently, the feed rate of the substrate must be substantially reduced which makes the processing device commercially unviable.

In light of the foregoing, there is a need for a particle beam processing device that operates more efficiently, is smaller in size, has a reduced power demand, and is cheaper to construct.

SUMMARY OF THE INVENTION

The advantages and purposes of the invention will be set forth in part in the description which follows, and in part will be obvious from the description, or may be learned by practice of the invention. The advantages and purposes of the invention will be realized and attained by the elements and combinations particularly pointed out in the appended claims.

To attain the advantages and in accordance with the purposes of the invention, as embodied and broadly described herein, one aspect of the invention is directed to a particle beam processing device that is smaller in size and more efficient. In accordance with the invention, the particle beam processing device comprises a power supply, a particle generating assembly, a foil support assembly, and a processing assembly. The particle generating assembly is located in an evacuated vessel and is connected to the power supply. The particle generating assembly operates at a first voltage in a range of 110 kVolts or less. The particle generating assembly includes at least one filament for generating a plurality of particles upon heating. The foil support assembly operates at a second voltage, which is higher than the first voltage, to permit at least a portion of the particles to travel from the first to the second voltage and exit the foil support assembly. The foil support assembly includes a thin foil made titanium or alloys thereof having a thickness of 10 micrometers or less. The processing assembly is for receiving the particles exiting the foil support assembly. The particles cause the chemical reaction on the substrate.

A second aspect of the invention is also directed to a particle beam processing device. Similar to the first aspect, the particle beam processing device comprises a power supply, a particle generating assembly, a foil support assembly, and a processing assembly, except that the foil support assembly includes a thin foil made aluminum or alloys thereof having a thickness of 20 micrometers or less.

A third aspect of the invention is directed to a method for causing a chemical reaction on a substrate in a particle beam processing device. The method comprises several steps including creating a vacuum in a particle generating assembly which has at least one filament, heating the filament(s) to create a plurality of particles, operating the particle generating assembly at a first voltage having a range of 110 kVolts or less, operating a foil support assembly having a thin foil at a second voltage, which is higher than the first voltage, to cause at least a portion of the particles to travel from the first voltage to the second voltage, and to exit the vacuum in the particle generating assembly, the thin foil being made of titanium or alloys thereof and having a thickness of 10 micrometers or less, and passing the exiting particles through the thin foil to enter a processing assembly where the substrate is being exposed to the particles.

A fourth aspect of the invention is also directed to a method for causing a chemical reaction on a substrate in a particle beam processing device. Similar to the third aspect, the method comprises the same steps except that the thin foil is made of aluminum or alloys thereof and having a thickness of 20 micrometers or less.

It is to be understood that both the foregoing general description and the following detailed description are exemplary and explanatory only and are not restrictive of the invention as claimed. Additional advantages will be set forth in the description that follows, and in part will be understood from the description, or may be learned by practice of the invention. The advantages and purposes may be obtained by means of the combinations set forth in the attached claims.

BRIEF DESCRIPTION OF THE DRAWINGS

The accompanying drawings, which are incorporated in and constitute a part of this specification, illustrate several embodiments of the invention and, together with the description, serve to explain the principles of the invention. In the drawings.

DESCRIPTION OF THE INVENTION

Reference will now be made in detail to several embodiments of methods and apparatus consistent with the invention, examples of which are illustrated in the accompanying drawings. Wherever possible, the same reference numbers will be used throughout the drawings to refer to the same or like parts. Moreover, the invention will be further clarified by the examples which follow.

A particle beam processing device according to the present invention can be made smaller in size and operates at a higher efficiency rate due to at least two inventive reasons; one, the operating voltage is reduced to 110 kVolts or less, and two, the thin foil, if it is made of titanium or alloys thereof, has a thickness of 10 micrometers or less, and if it is made of aluminum or alloys thereof, has a thickness of 20 micrometers or less.

In according with the principles of the present invention, a particle beam processing device comprises a power supply, a particle generating assembly, a foil support assembly, and a processing assembly.

Figure 1:
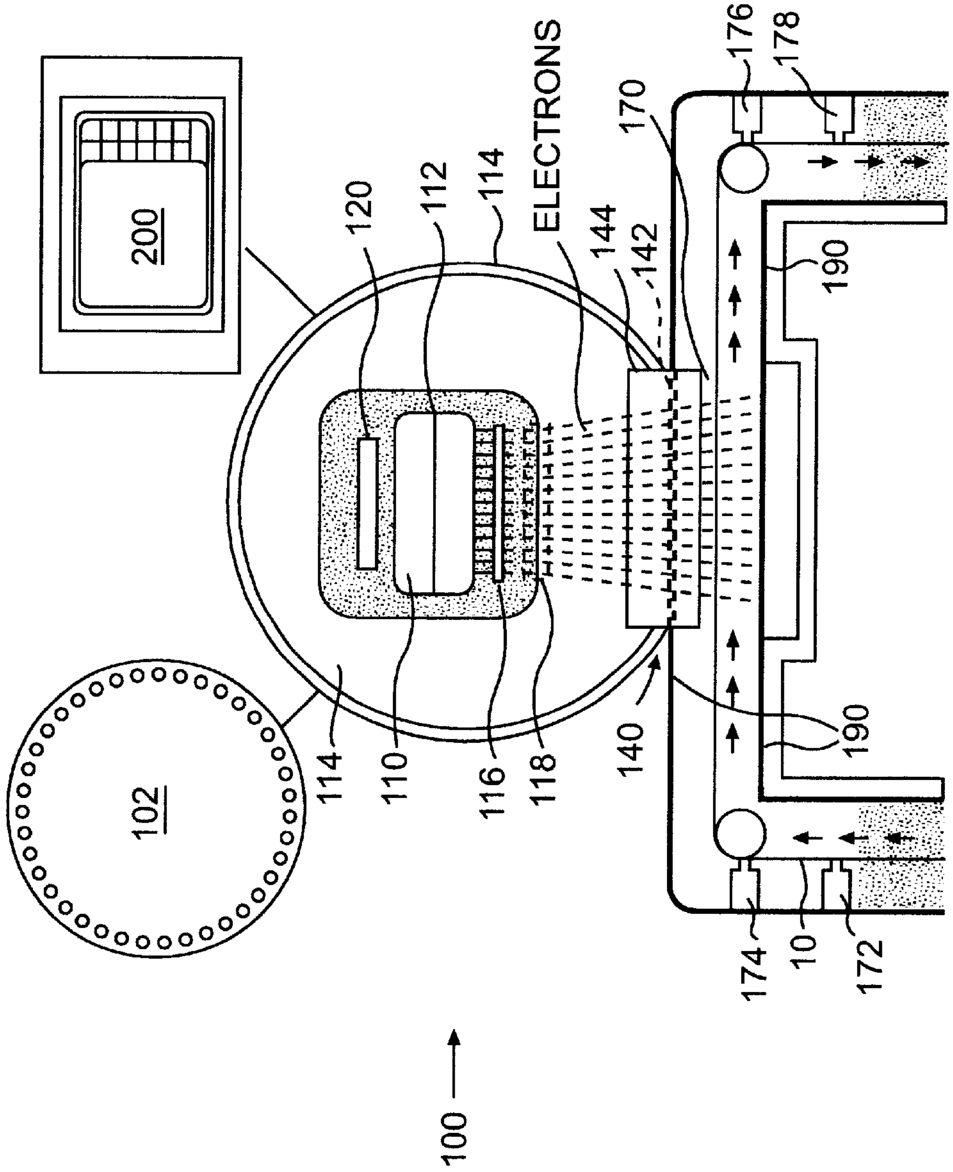
FIG. 1 is a schematic view of the particle beam processing device according to one embodiment of the present invention.

FIG. 1 schematically illustrates a particle beam processing device 100 consistent with the principles of this invention including power supply 102, particle beam generating assembly 110, foil support assembly 140, and processing assembly 170. Power supply 102 preferably provides an operating voltage of 110 kVolts or less, more preferably in a range of 90–100 kV, to the processing device 100. Power supply 102 may be of the type commercially available, which includes multiple electrical transformers located in an electrically insulated steel chamber to provide high voltage to particle beam generating assembly 110 to produce electrons.

Particle beam generating assembly 110 is preferably kept in a vacuum environment of vessel or chamber 114. In an embodiment where an electron beam is generated, i.e. an EB processing device, particle generating assembly 110 is commonly referred to as an electron gun assembly. Evacuated chamber 114 may be constructed of a tightly sealed vessel in which particles, such as electrons, are generated. Vacuum pump 212 (shown in FIG. 3) is provided to create a vacuum environment in the order of approximately $10^{-6}$ Torr. Inside the vacuum environment of chamber 114, a cloud of electrons are generated around filament 112 when high-voltage power supply 102 sends electrical power to heat up filament 112.

Filament 112 then glows white hot and generates a cloud of electrons. Electrons are then drawn from filament 112 to areas of higher voltage, since electrons are negatively charged particles, as described below and accelerated to extremely high speeds. Filament 112 may be constructed of one or more wire(s) commonly made of tungsten, and may be configured to be spaced evenly across the length of foil support 144 and emits electron beams across the width of substrate 10.

Figure 2:
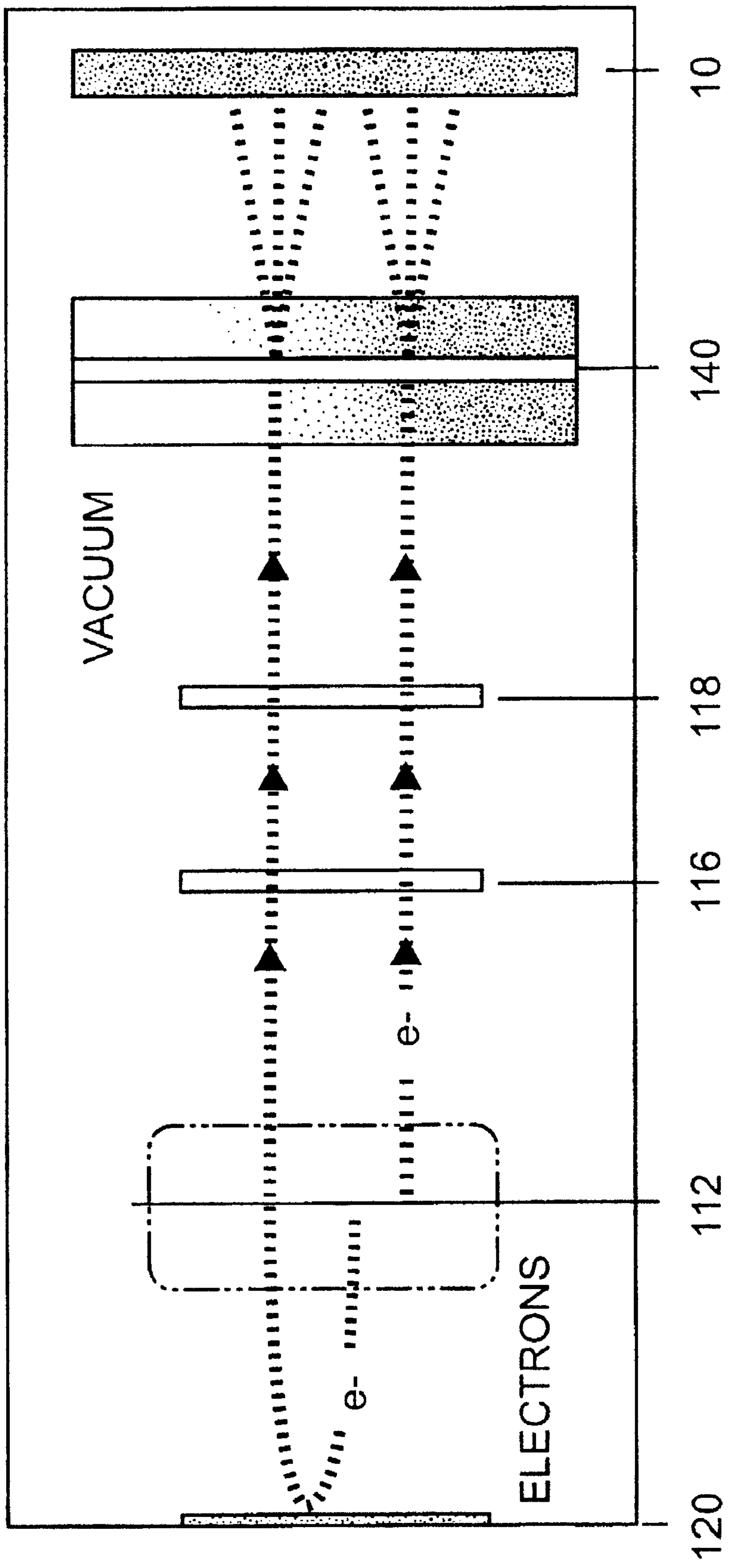
FIG. 2 is a schematic view of a voltage profile of an electron beam.

As shown in FIGS. 1 and 2, particle beam generating assembly 110 may include an extractor grid 116, a terminal grid 118, and a repeller plate 120. Repeller plate 120 repels electrons and sends the electrons toward extractor grid 116. Repeller plate 120 operates at a different voltage, preferably slightly lower, than filament 112 to collect electrons escaping from filament 112 away from electron beam direction as shown in FIG. 2.

Extractor grid 116, operating at a slightly different voltage, preferably higher than filament 112, attracts electrons away from filament 112 and guides them toward terminal grid 118. Extractor grid 116 controls the quantity of electrons being drawn from the cloud, which determines the intensity of the electron beam.

Terminal grid 118, operating generally at the same voltage as extractor grid 116, acts as the final gateway for electrons before they accelerate to extremely high speeds for passage through foil support assembly 140.

According to one embodiment of the present invention, for example, filament 112 may operate at −110,000 Volts and foil support assembly 140 may be grounded or set at 0 Volt. Repeller plate 120 may be selected to operate at −110,010 Volts to repell any electrons towards filament 112. Extractor grid 116 and terminal grid 118 may be selected to operate in a range of −110,000 Volts to −109,700 Volts.

The electrons then exit vacuum chamber 114 and enter the foil support assembly 140 through a thin foil 142 to penetrate a coated material or substrate 10 for the chemical reaction. The chemical reaction includes, for example, polymerization, crosslinking or sterilization. The speed of the electrons may be as high as or above 100,000 miles per second. Foil support assembly 140 may be made up of a series of parallel copper ribs (not shown). Thin foil 142, as shown in FIG. 1, is securely clamped to the outside of foil support assembly 144 to provide a leak-proof vacuum seal inside chamber 114. High speed electrons pass freely between the copper ribs, through thin foil 142 and into substrate 10 being treated. To prevent an undue energy loss, the foil is preferably made as thin as possible while at the same time providing sufficient mechanical strength to withstand the pressure differential between the vacuum state inside particle generating assembly 110 and processing assembly 170.

In accordance with the principles of this invention, the particle beam generating device can be made smaller in size and operate at a higher efficiency level when the thin foil of the foil support assembly is made of titanium or alloys thereof and having a thickness of 10 micrometers or less, preferably in a range of 3–10 micrometers, more preferably in a range of 5–8 micrometers. Alternatively, thin foil 142 may also be constructed of aluminum or alloys thereof having a thickness of 20 micrometers or less, preferably in a range of 6–20 micrometers, more preferably in a range of 10–16 mircometers.

Figure 3:
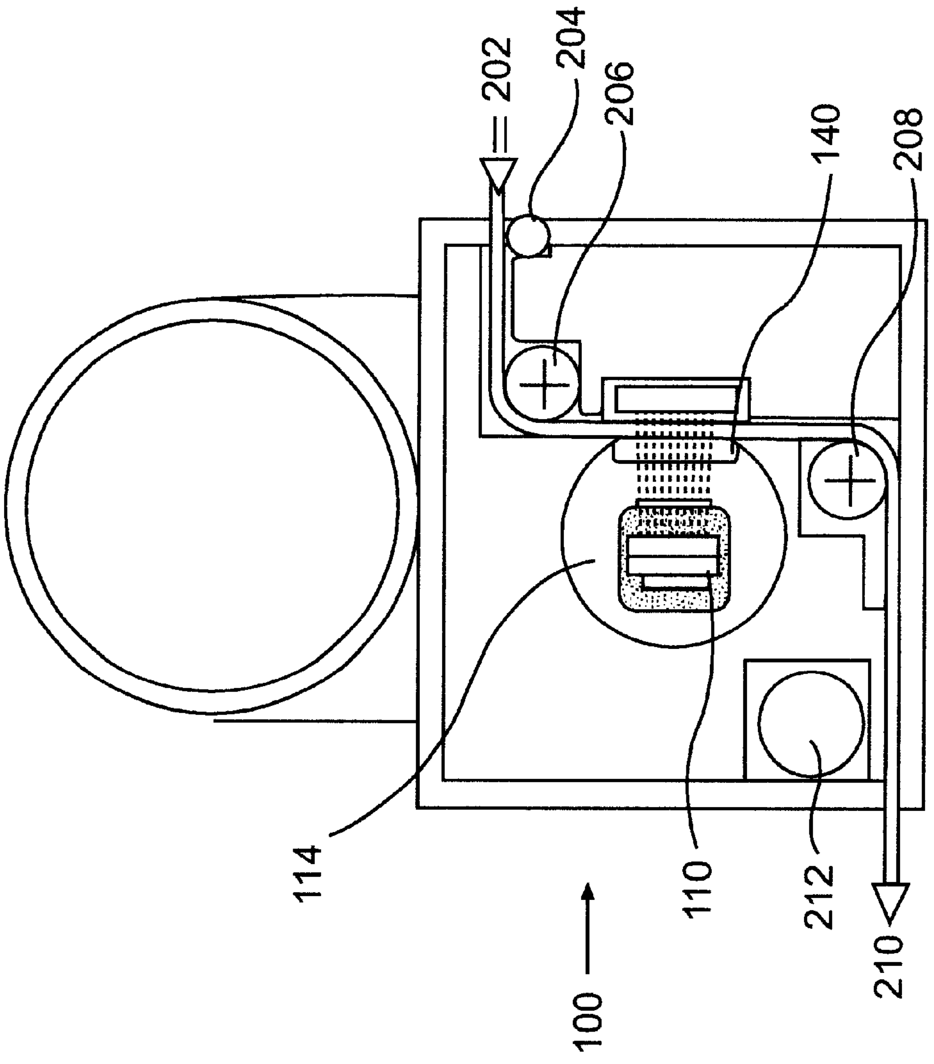
FIG. 3 is a front view of the particle beam processing device according to the preferred embodiment of the present invention.

Once the electrons exit the foil support assembly 140, they enter the processing assembly 170 where the electrons penetrate a coating or web substrate and cause a chemical reaction resulting in polymerization, crosslinking or sterilization. As shown in FIG. 3, the coating or web substrate is being fed into the processing device 100 to enter processing assembly 170. Processing assembly 170 includes a web entrance 202 where substrate 10 enters, rollers 204, 206, and 208 to guide and deliver substrate 10 through the processing assembly 170, and a web exit 210 where substrate 10 exits the processing device 100. The product being treated is instantaneously transformed, needs no drying or cooling and contains many new and desirable physical properties. Products can be shipped immediately after processing.

The particle beam processing device may include a protective lining surrounding at least a portion of the periphery of the device to absorb radiation, such as X-ray, emitted when the electrons decelerate as they are absorbed in matter.

As shown in FIG. 1, a protective lining 190 surrounds the periphery of processing device 100, such as evacuated chamber 114 and processing assembly 170. Protective lining 190 absorbs substantially all X-rays created when electrons decelerate in matter. The thickness and material selected for protective lining 190 form a function primarily determined by the desired absorption rate of the X-rays. In one embodiment, protective lining 190 is preferably capable of absorbing X-ray radiation at an absorption rate with residuals less than or equal to approximately 0.1 mrem/hour. The unit mrem/hour represents an absorption of 0.1 mili radiation equivalent to man per one hour. One milirem is equivalent to 1 milirad. One way to measure the radiation emitted is by measuring the absorption at a distance of 10 cm away from protective lining 190 by an instrument such as an ionization chamber instrument commercially known as Bicron RSO-5. To further enhance safety measure of particle beam processing device 100, a safety interlock switches (not shown) may be provided to ensure safe operation by automatically stopping production whenever interlocks are opened.

The particle beam processing device may further include a processor, such as a computerized microprocessor, to regulate the quantity of electrons generated so the electron beam output is proportional to the feeding speed of the substrate. As shown in FIG. 1, a process control system 200 is provided to control several processes including but not limited to maintaining the required vacuum environment, initiating system operation with predetermined voltages and filament power, synchronizing electron generation with process speed to maintain constant treatment level, monitoring functions and interlocks, and providing warnings and/or alarms whenever the system functions exceed set limits or an interlock problem is detected.

In operation, particle beam processing device 100 works as follows. A vacuum pump 212 (shown in FIG. 3) evacuates air from chamber 114 to achieve a vacuum level of approximately $10^{-6}$ Torr, at which point processing device 100 is fully operational. In particle generating assembly 110, particle gun assembly components, including repeller plate 120, extractor grid 116, and terminal grid 118, are set at three independently controlled voltages which initiate the emission of electrons and guide their passage through foil support 144.

During the particle beam processing, a combination of electric fields inside evacuated chamber 114 create a "push/pull" effect that guides and accelerates the electrons toward thin foil 142 of foil support 144, which is at ground (0) potential. The quantity of electrons generated is directly related to the voltage of extractor grid 116. At slow production speeds, extractor grid 116 is set at a lower voltage than at high speeds, when greater voltage is applied. As the voltage of extractor grid 116 increases, so does the quantity of electrons being drawn from filament 112.

The coatings to be cured, for example, inks, adhesives and other coatings, generally require a low oxygen environment to cause the chemical conversion from a liquid state into a solid state. Therefore, the particle beam processing device according to this invention may include, as illustrated in FIG. 1, a plurality of nozzles 172, 174, 176, and 178 distributed in processing zone 170 to inject gas other than oxygen to displace the oxygen therein. In one embodiment, nitrogen gas is selected to be pumped into processing zone 170 through nozzles 172, 174, 176, and 178 to displace the oxygen that would prevent complete curing.

As can be seen from the description above, particle beam processing device 100 can be calibrated to achieve extremely high precision specification because process control system 200 may be set to provide the exact depth level of cure desired on a substrate or coating. Process control system 200 calculates the dose and the depth of electron penetration into the coating or substrate. The higher the voltage, the greater the electron speed and resultant penetration.

Dose is the energy absorbed per unit mass and is measured in terms of megarads (Mrad), which is equivalent to 2.4 calories per gram. A higher number of electrons absorbed reflects a higher dose value. In application, dose is commonly determined by the material of the coating and the depth of substrate to be cured. For example, a dose of 5 Mrad may be required to cure a coating on a substrate that is made of rice paper and having a mass density of 20 gram/m$^2$. Dose is directly proportional to the operating beam current which is the number of electrons extracted, and inversely proportional to the feed speed of the substrate, as expressed by the following formula:

$$Dose=K\cdot(I/S)$$

whereby I is the current measured in mAmp, S is the feed speed of the substrate measured in feet/min, and K is a proportionality constant which represents a machine yield of the processing device, or the output efficiency of that particular processing device.

Figure 4:
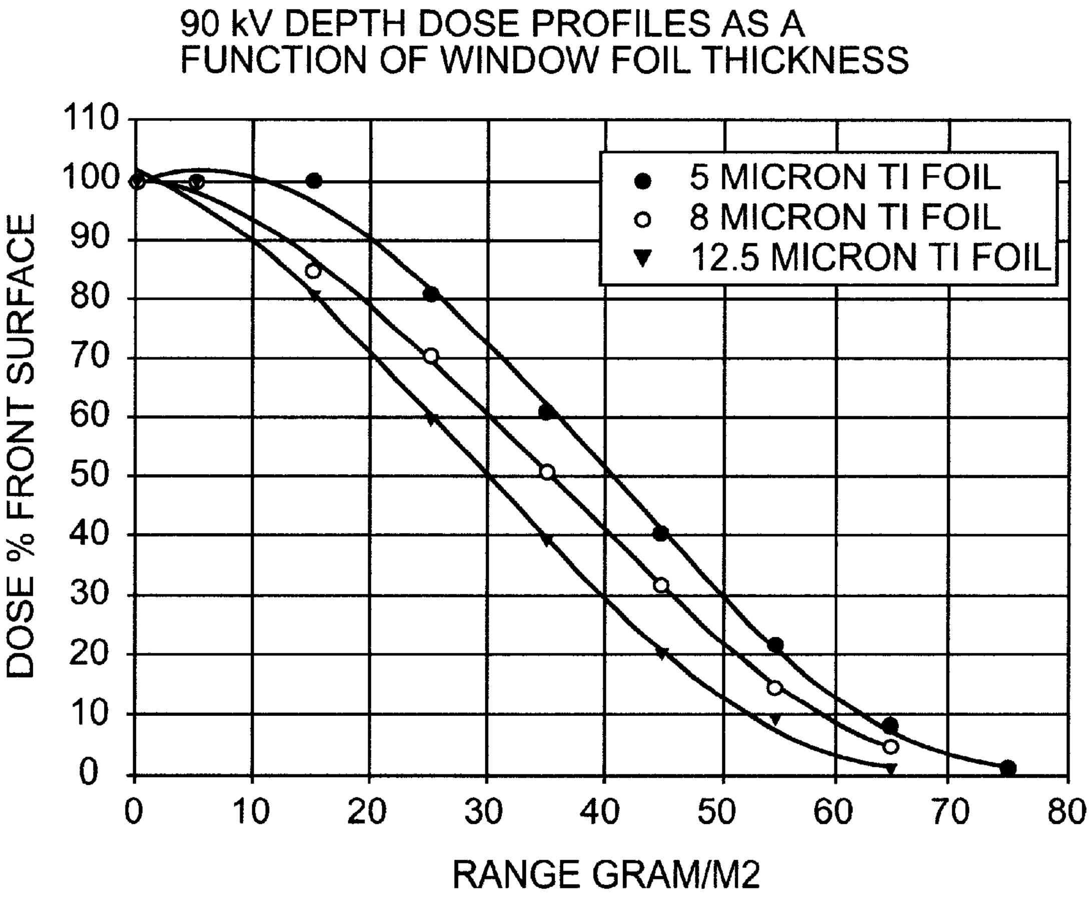
FIG. 4 is a chart of depth dose profiles as a function of thickness of titanium foil measured at an operating voltage of 90 kV.
Figure 5:
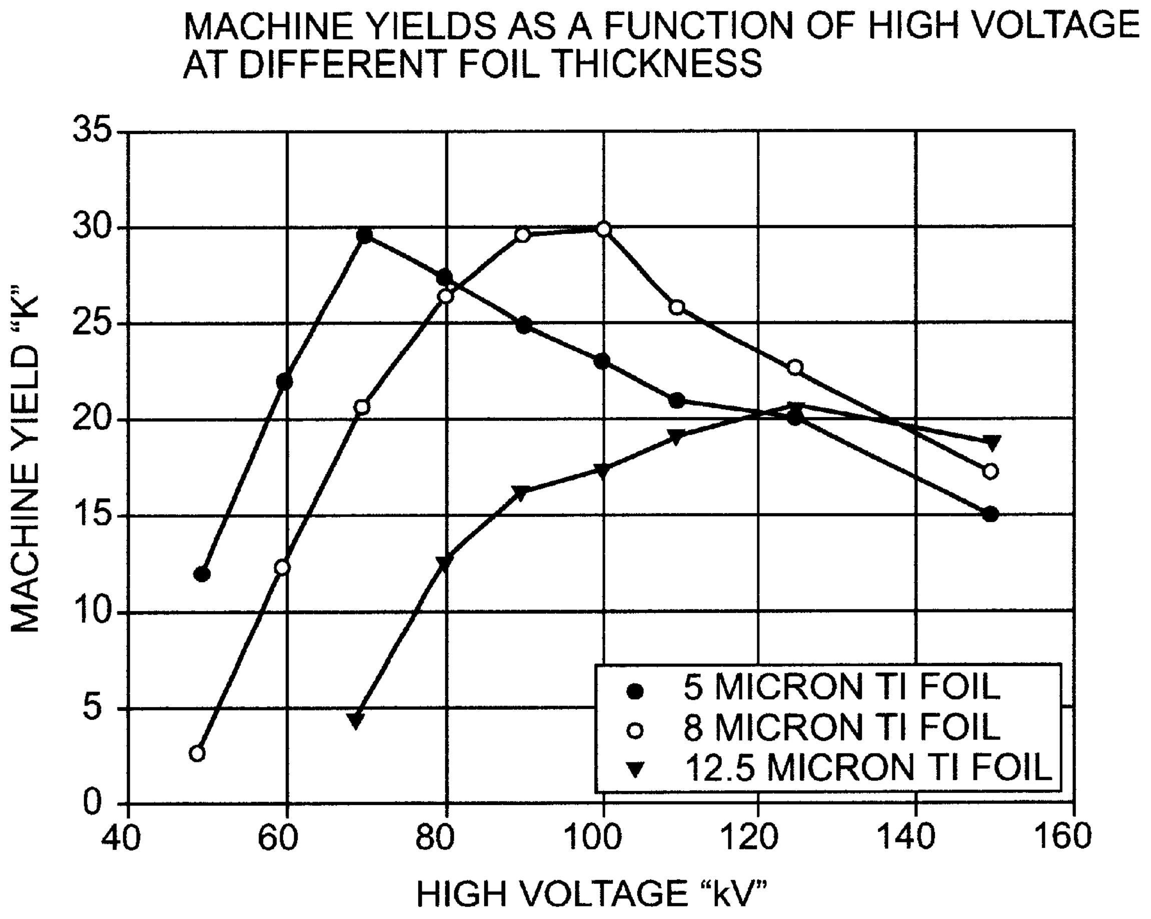
FIG. 5 is a chart of machine yields for a processing device having a width of 1.5 feet as a function of operating voltage measured using titanium foil thicknesses of 5, 8, and 12.5 micrometers.
Figure 6:
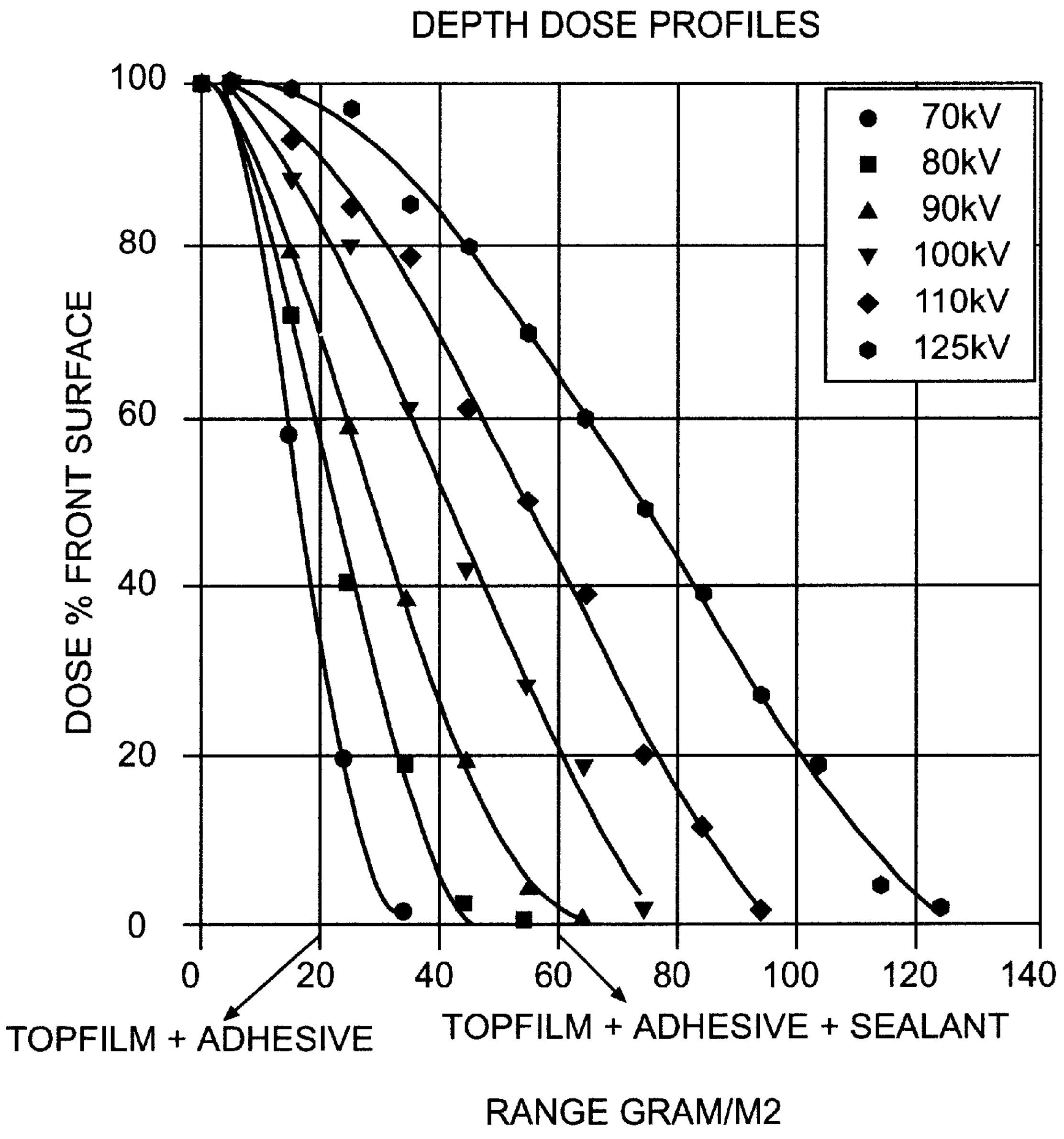
FIG. 6 is a chart of depth dose profiles as a function of thickness of titanium foil measured at various operating voltages.
Figure 7:
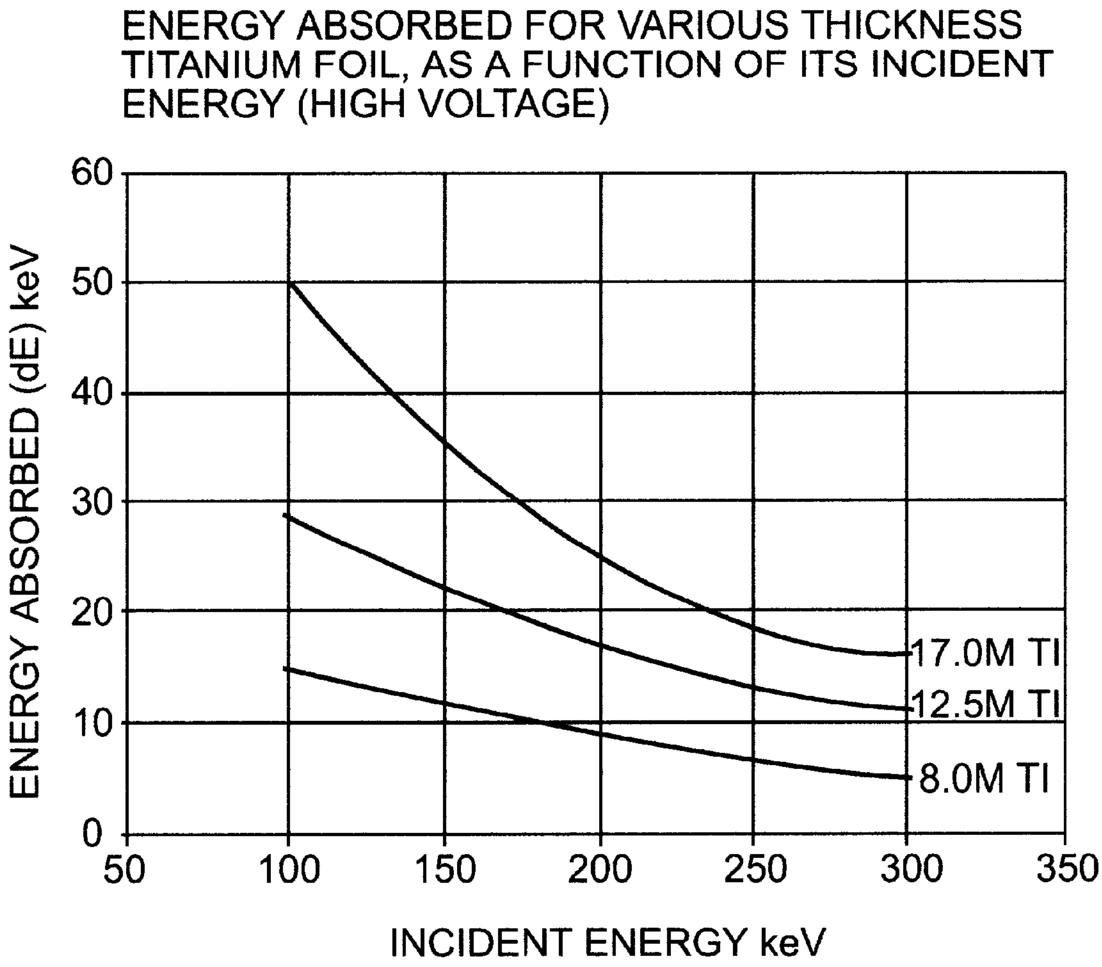
FIG. 7 is a chart of energy absorbed by the thin foil as a function of the incident energy in keV measured using titanium foil thicknesses of 17, 12.5, and 8 micrometers.

The following examples as illustrated in the charts shown in FIGS. 4–7 are provided as a result of a series of experiments. FIG. 4 illustrates the relationship between depth dose profiles and mass density of the coatings with respect to three different thicknesses of the thin foil as measured at an operating voltage of 90 kV. FIG. 5 illustrates the relationship between operating voltage ("High Voltage") as measured in kVolts and the machine yield K for a processing device having a width of 1.5 feet with respect to thin foil made of titanium having thicknesses of 5, 8, and 12.5 micrometers. FIG. 6 illustrates the relationship between depth dose profiles and mass density of the coatings with respect to various operating voltages. FIG. 7 illustrates the relationship between energy absorbed by the thin foil ("dE") measured in keV and incident energy or operating voltage measured in keV with respect to three titanium foil having thickness of 17, 12.5, and 8 micrometers.

The goal of the present invention is to increase the output efficiency of the processing device by applying an operating voltage that is as low as possible to reduce the power needed to generate the operating voltage which makes the processing device more compact and cheaper to build. Thus, as shown in the depth dose profiles of FIG. 6, the optimum curve preferably moves closer towards an imaginary vertical line crossing the X-axis representing the density of the Coating to be cured. However, as previously discussed in the Description of the Related Art, reducing the operating voltage causes a tremendous heat problem which renders the processing device not commercially viable. As illustrated in FIGS. 4 and 7, heat problem can be solved by utilizing a titanium foil that has a thickness of 10 micrometers or less.

The data taken in these experiments was measured utilizing thin film dosimetry techniques. Dosimetry techniques involve nylon films which have thicknesses in the range of 9–10 micrometers. The dosimeters contain a radiochromic dye that changes color from colorless to blue when the dye is exposed to electromagnetic radiation. The intensity of the blue color is directly proportional to the amount of radiation exposure obtained from the nylon films. By measuring the intensity or optical density of the blue color using a densitometer, one can convert the measured optical density to the absorbed dose in Mrads. The conversion from optical density to dose in Mrads is achieved by prior calibration of the dosimeters and the densitometer using $Co^{60}$ Gamma facility at the National Institute of Standards and Technology, Gaithersburg, Md. These experiments utilized Dosimeters Model FWT-60-810 manufactured by Far West Technology, Goleta, Calif. and Densitometer Model 92 SXN 3285 manufactured by Far West Technology, Goleta, Calif.

EXAMPLE 1

The result of a first experiment, shown in FIG. 4, indicates that particle beam processing device 100 using thin foil 142 that is made of titanium having a thickness of less than 12.5 micrometer improves the electron penetration in substrate 10.

In the first experiment, thin film nylon dosimeters were used to measure the penetration capability of electrons. The parameters for this experiment include: a constant operating voltage of 90 kV, a dose of 5 Mrads, and a thin titanium foil. Three specimens were tested to study three different titanium foil thicknesses of 12.5, 8, and 5 micrometers, one for each foil thickness.

The three specimens were made of thirty dosimeters, each having a surface area of approximately 2×2cm$^2$. These dosimeters were divided into three stacks, each stack containing an arrangement of ten dosimeters one on top of the other. One edge of each stack of dosimeters was taped to a polyester carrier having a thickness of 125 micrometer. The three polyester carriers were then taped to a paper substrate and fed through processing device 100 to receive radiation treatment. The first stack was treated in processing device 100 with 12.5 micrometer titanium foil; the second stack with 8 micrometers, and the third stack with 5 micrometers. Following the radiation treatment, the three stacks were annealed in an oven at 60° C. for 5 minutes. The dosimeters were then separated, individually measured on the densitometer, and converted to dose in terms of Mrads. For each stack, the dose values obtained were normalized to the first dosimeter.

FIG. 4 shows the data resulted from this experiment with the Y-axis representing the normalized dose for each stack and the X-axis representing the mass density in terms of gram/m$^2$. The mass density was obtained by measuring the dosimeters mass density that resulted in 10 grams/m$^2$. It is assumed that the first point is at one half of the mass density, and then each mass density is added to it for subsequent points. This experiment concludes that the thinner the foil is used in particle beam processing device 100, the higher electron penetration on substrate 10 is achieved,

EXAMPLE 2

The result of a second experiment, shown in FIG. 5, teaches that thinner foil, not only improves electron penetration on a substrate, but also increases the efficiency or machine yield K.

In the second experiment, similar to the first experiment, thin film nylon dosimeters were used to measure the machine yield K of a processing device having a width of 1.5 feet at various operating voltages measured in kV. Three measurements were run to study three different titanium foil having thicknesses of 12.5, 8, and 5 micrometers.

The value of machine yield K was obtained by calculating the average of nine individual dosimeter chips. Each dosimeter of 2×2 cm$^2$ was taped on one edge to a polyester carrier. Each polyester carrier contained nine dosimeters. The polyester carrier was taped to the paper substrate and fed through processing device 100 to receive radiation treatment. After irradiation the dosimeters were annealed at 60° C. for 5 minutes. Thereafter, the optical density and the dose value were measured. For each measurement, processing device 100 was set to deliver 4 Mrads to the dosimeters. Processing device 100 included several gauges (not shown) to indicate the feed rate of the substrate in feet/minute and the current of the particle beam in mAmp. The average dose was determined and used to calculate the K value according to the following equation:

$$K\,(\text{Mrads-feet/min/mAmp}) = \frac{\text{Dose (Mrads)} \times \text{Speed (feet/min)}}{\text{Current (mAmps)}}$$

The same procedure was repeated for all voltages.

FIG. 5 shows the data resulted from this experiment with the Y-axis representing the machine yield K and the X-axis representing the operating voltages in kV. This experiment concludes that thinner foil increases the efficiency or machine yield K. Machine yield K of the processing device in accordance with the present invention increases, and reaches an optimum value at the corresponding optimum operating voltage. For example, when an 8 micrometer titanium foil is used and the processing device operates at 100 kVolts, the machine yield reaches approximately 30 at 90–100 kVolts. Similarly, when a 5 micrometer titanium foil is used and the processing device operates at 70 kVolts, the machine yield reaches almost 30. Comparing the machine yield K between the processing device using 12.5 micrometer titanium foil and the processing devices using 8 and 5 micrometers titanium foils, the following relationship is deduced:

$$20=30/L$$

wherein L is the width of the processing device measured in feet, in this case 1.5 feet at an operating voltage of 125 kVolts.

EXAMPLE 3

The result of a third experiment, as shown in FIG. 6, illustrates one advantage of operating processing device 100 at a voltage of 110 kV or less in the field of Flexible Food Packaging.

In the third experiment, depth dose profiles for processing device 100 at various operating voltages were measured according to the procedure described earlier with respect to the first experiment. A typical application of Flexible Food Packaging is the packaging for processed meat and cheese which commonly include three layers top film, adhesive, and sealant. For example, Table 1 below provides a typical packaging layers and their thicknesses:

TABLE 1

| | |
|---|---|
| Top film of 0.5 mil polyester type (PET): | 17.0 gram/$m^2$ |
| Adhesive: | 3.0 gram/$m^2$ |
| Sealant of polyethylene copolymer: | 40.0 gram/$m^2$. |

Electron beam has generally been used to cure the adhesive in between the top film and the sealant.

As illustrated in FIG. 6, EB processing device currently available in the market, which operates at 125 kV, sufficiently cured the adhesive at a depth of 20 gram/$m^2$, curing the top film and the adhesive. However, it deposited significant dose to the sealant layer at a depth of 60 gram/$m^2$ (top film, adhesive, and sealant). The polyethylene based sealant layer, which contacts the food being packaged, emits undesirable odors when it absorbs the dose deposited thereon. In addition, the deposited dose also increases the seal initiation temperatures, thus making it difficult to heat seal. These two effects on the sealant layer prevent the current EB processing device from meeting the demands for flexible food packaging industry.

Processing device 100 consistent with the principles of the present invention overcomes the problems of prior processing device by operating at a voltage range of 110 kV or less, preferably 90–100 kV, at a commercially viable substrate feed rate. As shown in FIG. 6, at the operating voltage of 110 kV or less, one can properly cure the adhesive at a depth of 20 gram/$M^2$, yet impart significantly less dose, and thus cause less damage to the sealant film.

EXAMPLE 4

The result of a fourth experiment, as shown in FIG. 7, describes the relation between the energy absorbed by the titanium foil as a function of its operating voltage measured in kVolts. This study compared three different titanium foil thicknesses of 17, 12.5, and 8 micrometers. The studies on the 17 and 12.5 micrometers were performed at the National Institute of Standards and Technology according to the electron energy dissipation in titanium foil using Monte-Carlo calculations. Based on the data resulted from these studies, data for the 8 micrometer titanium foil was extrapolated. This study confirms that thinner foil absorbs less energy, especially at lower voltages. Therefore, a processing device utilizing foil having a thickness of 10 micrometers or less solves the heat management problem since energy absorbed by the foil converts to power resulting in heat management issues with the foil.

Because the processing device according to the present invention can operate at an operating voltage of 110 kVolts or less, not only that the size of power supply to generate the operating voltage can be reduced, but also the size of evacuated vessel to contain the particle beam generating assembly can be substantially reduced. Furthermore, the thickness of protective lining can be reduced because less severe radiation is emitted by the electrons exiting the evacuated vessel at a slower rate when the operating voltage is 110 kVolts or less.

In application, a particle beam processing device may be used in a manufacturing process, such as electron beam (EB) processing, to treat a substrate or a coating exposed to the device. The treatment may include a chemical reaction, such as polymerization, crosslinking, or sterilization. When the substrate or coating is exposed to highly accelerated electrons, a reaction occurs in which the chemical bonds in the substrate or coating are broken and a new, modified molecular structure is formed. This application applies broadly to any particle beam, but for exemplary purposes, the electron beam is particularly described. The following will describe possible chemical reactions that could occur during EB processing.

EXAMPLE 5

Figure 8:
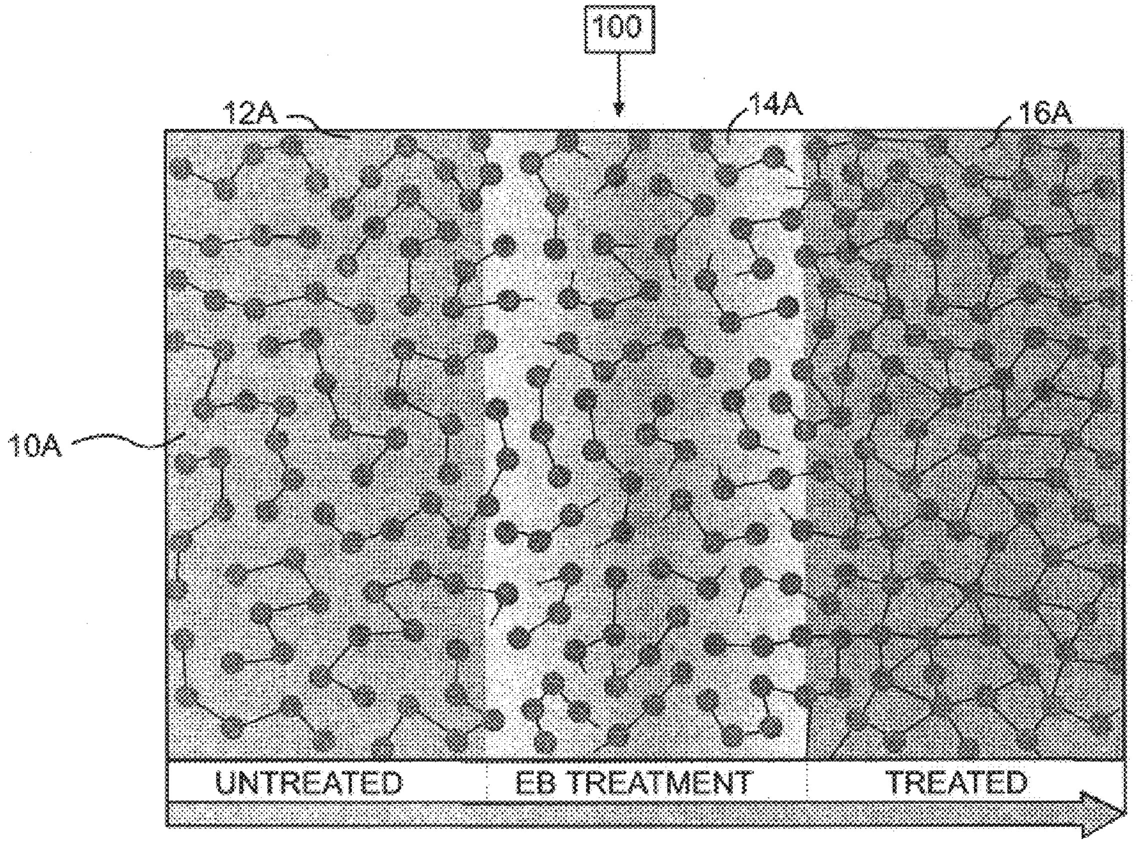
FIG. 8 is a schematic view of a crosslinking reaction on a substrate as the substrate passes through a particle beam processing device.

Crosslinking is a chemical reaction that alters and enhances the physical characteristics of the material being treated. In a crosslinking process, an interconnected network of chemical bonds or links develops between large polymer chains to form a stronger molecular structure. Application of EB processing by crosslinking reaction includes, for example, when a product like plastic film or rubber substrate is treated with electrons, the large polymers in these products develop many linking bonds. These bonds increase the product's performance and its resistance to weakening at elevated temperatures. FIG. 8 illustrates the crosslinking reaction on substrate 10A as substrate 10A passes under the particle beam processing device, schematically referred to as 100, from an untreated state on the left area 12A, into an exposure area 14A, to a treated state on the right area 16A.

EXAMPLE 6

Figure 9:
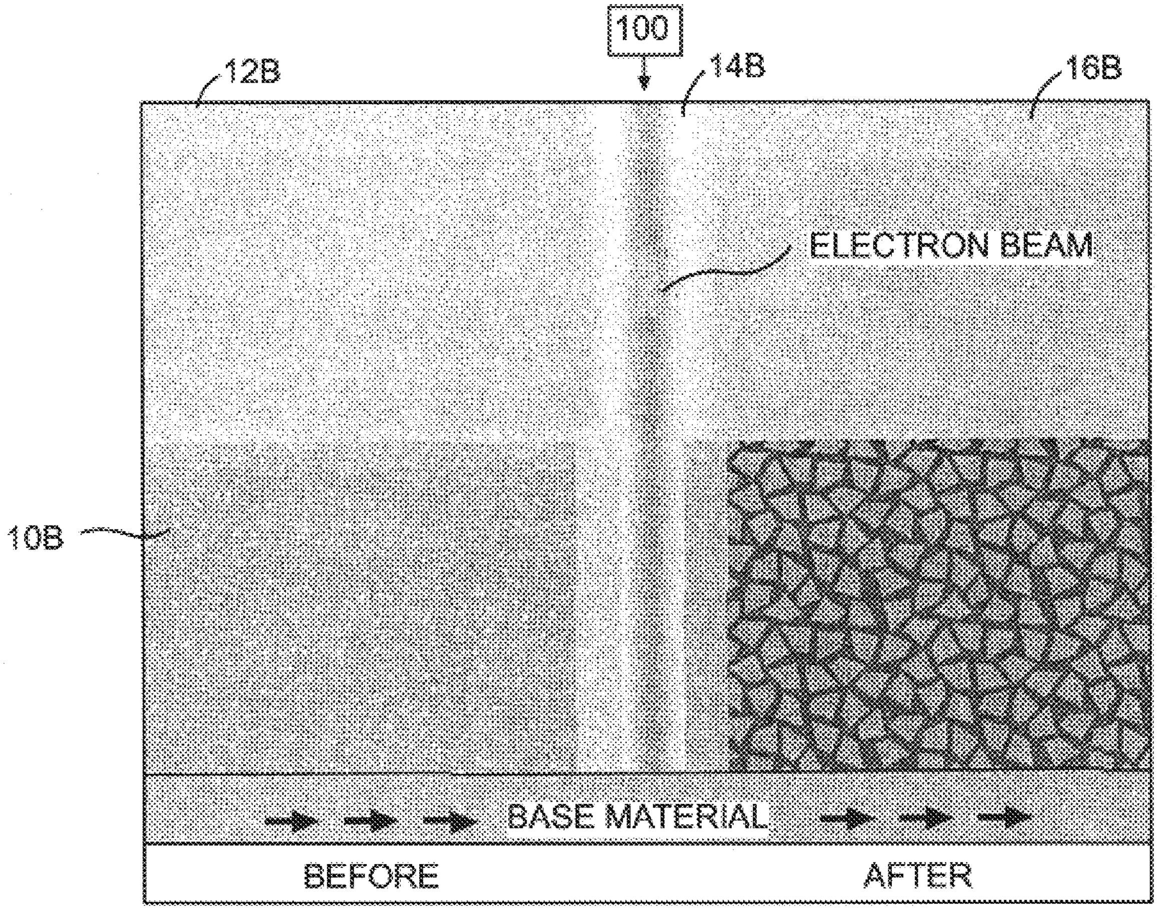
FIG. 9 is a schematic view of a polymerization reaction on a substrate as the substrate passes through the particle beam processing device.

Like crosslinking, polymerization is a process in which several individual groups of molecules combine together to form one large group called a polymer. This causes significant physical changes in the product being treated and results in many desirable physical characteristics such as high gloss and abrasion resistance. For example, when exposed to accelerated electrons during EB processing, furniture coatings and adhesives are transformed almost instantaneously from a liquid (uncured) state into a non-tacky (cured) solid state. FIG. 9 illustrates the polymerization reaction on substrate 10B as substrate 10B passes under particle beam processing device 100, from an untreated state on the left area 12B, into an exposure area 14B, to a treated state on the right area 16B.

EXAMPLE 7

Figure 10:
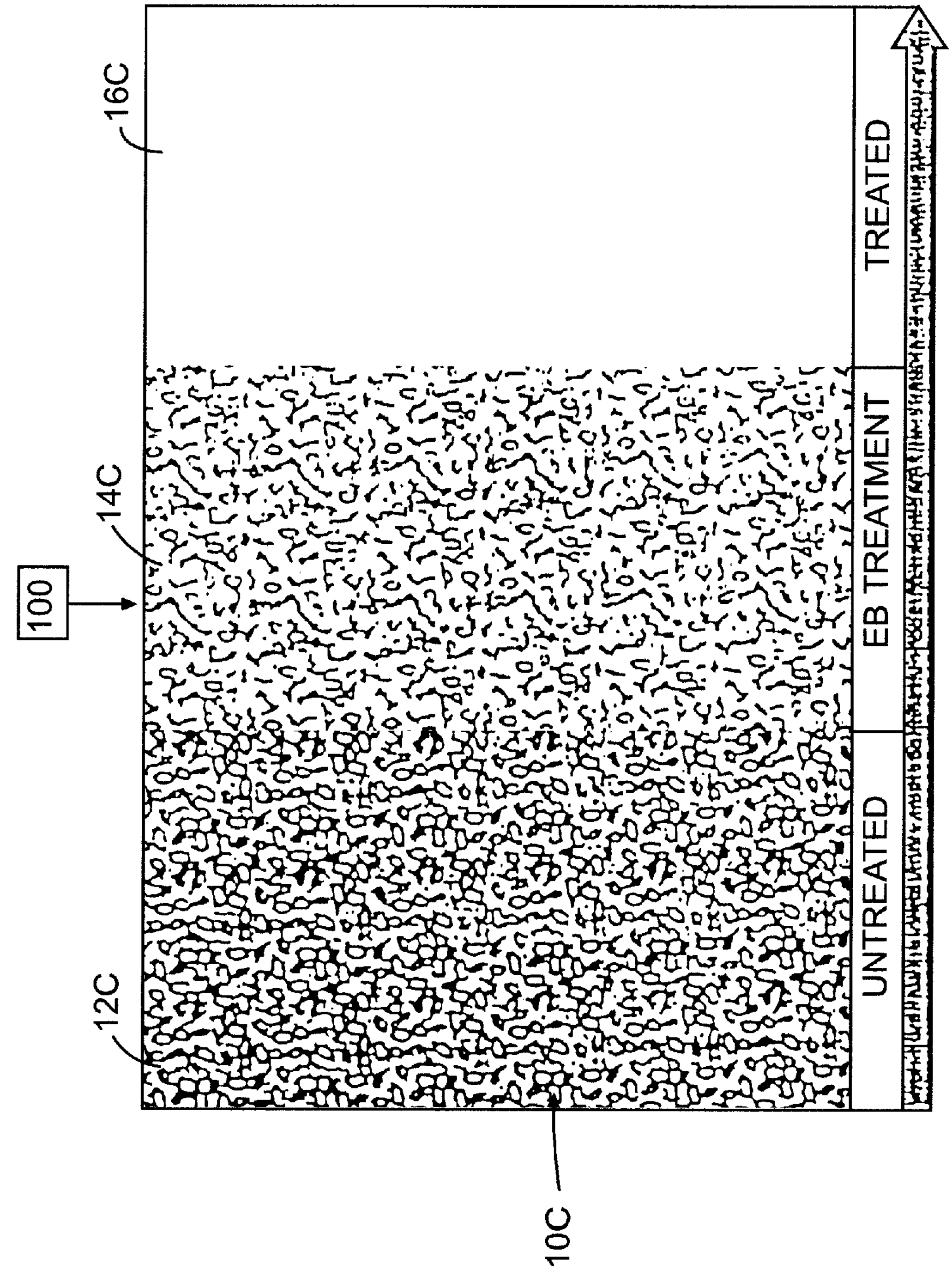
FIG. 10 is a schematic view of a sterilization reaction on a substrate as the substrate passes through the particle beam processing device.

Sterilization is a process of destroying contaminating microorganisms by rendering them sterile or unable to reproduce. EB sterilization occurs when electrons are directed into the microorganisms whereby breaking the DNA chains which control reproduction, Once a product has been sterilized, no microbial decomposition can take place. Since electrons act as a physical sterilizing agent rather than a chemical one, they do not change the chemistry of the target product or leave any residual chemicals. EB sterilization offers a number of advantages over chemical sterilization techniques, such as those that use hydrogen peroxide and ethylene oxide. For example, EB sterilization may be used to sterilize medical supplies and sensitive food products as well as their respective packaging, whereas chemical sterilization could not be used. FIG. 10 illustrates the sterilization reaction on substrate 10C as substrate 10C passes under particle beam processing device, schematically referred to as 100, from an untreated state on the left area 12C, into an exposure area 14C, to a treated state on the right area 16B.

The process described above offers several advantages, such as, the particle beam processing happens virtually instantaneously, commonly operates at room temperature and produces no emissions or air pollution since particle beam coating materials are solids. In addition, the coatings do not contain harmful solvents or volatile organic compounds.

It will be apparent to those skilled in the art that various modifications and variations can be made in the particle generating assembly, foil support, processing zone, and process control system, as well as the materials chosen for the thin foil, the filaments or particle generating components, and in construction of the particle beam processing system as well as other aspects of the invention without departing from the scope or spirit of the invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims and their equivalents.

We claim:

1. A particle beam processing device being smaller in size and having higher efficiency that causes a chemical reaction on a substrate, comprising:

a power supply;

a particle generating assembly located in an evacuated vessel and connected to the power supply operating at a first voltage in a range of 110 kVolts or less, the particle generating assembly including at least one filament for generating a plurality of particles upon heating;

a foil support assembly operating at a second voltage, which is higher than the first voltage, to permit at least a portion of said particles to travel from the first to the second voltage and exit the foil support assembly, the foil support assembly comprising a thin foil made of titanium or alloys thereof having a thickness of 10 micrometers or less; and a processing assembly for receiving said particles exiting the foil support assembly for use to cause said chemical reaction;

wherein a machine yield (K) of the processing device is determined by Dose representing energy absorbed per unit mass, Speed representing a feeding rate of the processing device, and Current representing a number of electrons extracted from the heated filament, according to:

$$K = \frac{\text{Dose} \cdot \text{Speed}}{\text{Current}}$$

wherein the machine yield (K) is above 30/L where L is the machine width measured in feet, and whereby:

K is machine yield measured in Mrads.feet/min/mAmp,

Dose is energy absorbed per unit mass measured in Mrads,

Speed is feed rate of the substrate measured in feet/min, and

Current is a number of electrons extracted from filament measured in mAmp.

2. The particle beam processing device of claim 1, wherein the evacuated vessel has an operating volume in a range of 0.05–145 $ft^3$.

3. The particle beam processing device of claim 1, wherein the at least one filament is constructed of wire such as tungsten or tungsten alloy and is spaced across a length of the foil support assembly.

4. The particle beam processing device of claim 1, wherein the particle generating assembly further comprises:

a first grid to control a quantity of the plurality of particles being drawn from the at least one filament, the first grid being operated at a third voltage which is higher than the first voltage.

5. The particle beam processing device of claim 4, wherein the particle generating assembly further comprises:

a second grid positioned adjacent the first grid and operating at the first voltage, the second grid acting as a gateway for the particles before accelerating from the first voltage to the second voltage.

6. The particle beam processing device of claim 1, wherein the foil support assembly comprises a plurality of openings to pass the plurality of particles out of the evacuated vessel and into the processing assembly.

7. The particle beam processing device of claim 1, wherein the processing assembly comprises:

a plurality of gas inlets to inject gas to complete the chemical reaction.

8. The particle beam processing device of claim 7, wherein the gas injected into the processing assembly comprises:

gas other than oxygen to displace oxygen existing in the processing assembly.

9. The particle beam processing device of claim 1, further comprising:

a protective lining surrounding at least a portion of the periphery of the particle beam processing device.

10. The particle beam processing device of claim 9, wherein the protective lining is capable of absorbing radiation with residuals less than or equal to 0.1 mrem per hour.

11. A particle beam processing device being smaller in size and having higher efficiency that causes a chemical reaction on a substrate, comprising:

a power supply;

a particle generating assembly located in an evacuated vessel and connected to the power supply operating at a first voltage in a range of 110 kVolts or less, the particle generating assembly including at least one filament for generating a plurality of particles upon heating;

a foil support assembly operating at a second voltage, which is higher than the first voltage, to permit at least a portion of said particles to travel from the first to the second voltage and exit the foil support assembly, the foil support assembly comprising a thin foil made of aluminum or alloys thereof having a thickness of 20 micrometers or less; and a processing assembly for receiving said particles exiting the foil support assembly for use to cause said chemical reaction;

wherein a machine yield (K) of the processing device is determined by Dose representing energy absorbed per unit mass, Speed representing a feeding rate of the processing device, and Current representing a number of electrons extracted from the heated filament, according to:

$$K = \frac{\text{Dose} \cdot \text{Speed}}{\text{Current}}$$

wherein the machine yield (K) is above 30/L where L is the machine width measured in feet, and whereby:

K is machine yield measured in Mrads.feet/min/mAmp,

Dose is energy absorbed per unit mass measured in Mrads,

Speed is feed rate of the substrate measured in feet/min, and

Current is a number of electrons extracted from filament measured in mAmp.

12. The particle beam processing device of claim 11, wherein the evacuated vessel has an operating volume in a range of 0.05–145 ft.

13. The particle beam processing device of claim 11, further comprising:

a protective lining surrounding at least a portion of the periphery of the particle beam processing device, the protective lining being capable of absorbing radiation with residuals less than or equal to 0.1 mrem per hour.

* * * * *

UNITED STATES PATENT AND TRADEMARK OFFICE

CERTIFICATE OF CORRECTION

PATENT NO. : 6,426,507 B1
DATED : July 30, 2002
INVENTOR(S) : Im Rangwalla et al.

It is certified that error appears in the above-identified patent and that said Letters Patent is hereby corrected as shown below:

Column 12,
Line 24, "Mrads.feet/min/" should read -- Mrads·feet/min/ --.

Column 14,
Line 11, "Mrads.feet/min/" should read -- Mrads·feet/min/ --.
Line 21, "ft." should read -- $ft^{3.}$ --.

Signed and Sealed this

Nineteenth Day of November, 2002

*Attest:*

JAMES E. ROGAN

*Attesting Officer*

*Director of the United States Patent and Trademark Office*